US00PP23904P2

(12) United States Plant Patent
Sakaue

(10) Patent No.: US PP23,904 P2
(45) Date of Patent: Sep. 17, 2013

(54) ***CAMPSIS* PLANT NAMED 'TAKARAZUKA ZUJIN'**

(50) Latin Name: *Campsis×tagliabuana*
Varietal Denomination: Takarazuka Zujin

(76) Inventor: Koichi Sakaue, Takarazuka (JP)

( * ) Notice: Subject to any disclaimer, the term of this patent is extended or adjusted under 35 U.S.C. 154(b) by 100 days.

(21) Appl. No.: 13/385,116

(22) Filed: Feb. 2, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Campsis* hybrid, 'Takarazuka Zujin', characterized by its dark green, clean foliage, its flowers that are coral-red in color with a yellow-orange throat, its compact, upright vining plant habit with good suitability as a container plant and its long bloom season, blooming from April to August in Japan.

2 Drawing Sheets

Botanical classification: *Campsis×tagliabuana*.
Variety denomination: 'Takarazuka Zujin'.

CROSS REFERENCE TO RELATED APPLICATIONS

This application is co-pending with U.S. Plant Patent Applications related to plants derived from the same breeding program. The Applications are entitled; *Campsis* Plant Named 'Takarazuka Fresa' (U.S. Plant patent application Ser. No. 13/385,119) and *Campsis* Plant Named 'Takarazuka Yellow' (U.S. Plant patent application Ser. No. 13/385,122).

BACKGROUND OF THE INVENTION

The present invention relates to a new and distinct cultivar of *Campsis×tagliabuana* (*C. grandiflora×C. radicans*) and will be referred to hereafter by its cultivar name, 'Takarazuka Zujin'. 'Takarazuka Zujin' is a new cultivar of perennial vine for use as a landscape plant.

'Takarazuka Zujin' originated as a seedling that arose from seed planted from an open pollination of unnamed plants of *Campsis×tagliabuana* from the Inventor's breeding line in Shizuoka Prefecture Takarazuka, Japan in 1995. The parents are therefore unknown. The new *Campsis* was selected as a single unique plant in 2000.

Asexual reproduction of the new cultivar was first accomplished by the Inventor using softwood stem cuttings in 2008 in Takarazuka, Japan. The characteristics of the new cultivar have been determined to be stable and are reproduced true to type in successive generations.

SUMMARY OF THE INVENTION

The following traits have been repeatedly observed and represent the characteristics of the new cultivar as grown outdoors in trial beds and in containers in Takarazuka, Japan. These attributes in combination distinguish 'Takarazuka Zujin' as a unique cultivar of star *Campsis*.

1. 'Takarazuka Zujin' exhibits dark green, clean foliage.
2. 'Takarazuka Zujin' exhibits flowers that are coral-red in color with a yellow-orange throat.

3. 'Takarazuka Zujin' exhibits a very compact, upright vining plant habit with good suitability as a container plant.
4. 'Takarazuka Zujin' exhibits a long bloom season, blooming from April to August in Japan.

'Takarazuka Zujin' can be most closely compared to cultivars derived from the same breeding program; 'Takarazuka Fresa' and 'Takarazuka Yellow'. 'Takarazuka Fresa' differs from 'Takarazuka Zujin' in having flowers that are red in color, in having a less compact plant habit and in commencing bloom later in the season. 'Takarazuka Yellow' differs from 'Takarazuka Zujin' in having flowers that are larger and peach orange to yellow in color. 'Takarazuka Zujin' can also be compared to the cultivars 'RUTCAM' (U.S. Plant Pat. No. 19,415) and 'HOMR' (U.S. Plant Pat. No. 18,394). 'RUTCAM' differs from 'Takarazuka Zujin' in flowers that are deeper red in color, in having a less compact plant habit and in having pubescent leaves. 'HOMR' differs from 'Takarazuka Zujin' in having flowers that are pinkish red in color and in having pubescent leaves and stems.

BRIEF DESCRIPTION OF THE DRAWING

The accompanying colored photograph illustrates the overall appearance and distinct characteristics of a one year-old plant of the new *Campsis* as grown outdoors in a one-gallon container in Takarazuka, Japan.

The photograph in FIG. 1 provides a view of a cluster of flowers of 'Takarazuka Zujin'.

Figure 1:
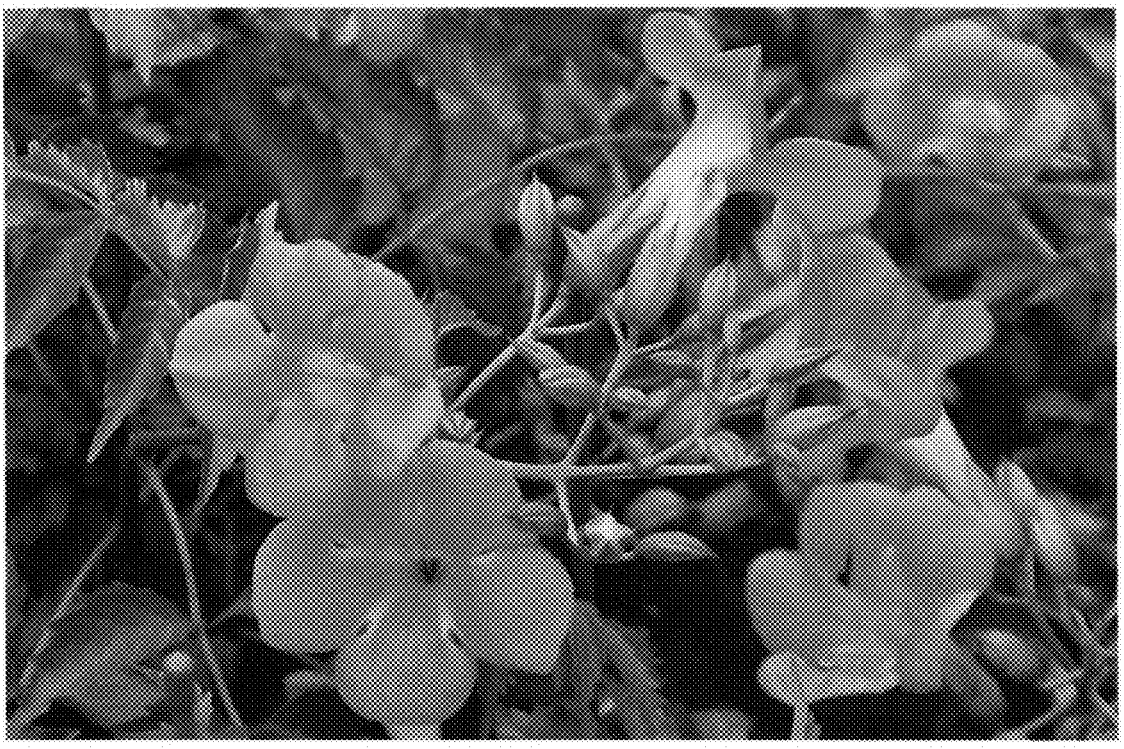
Figure 2:
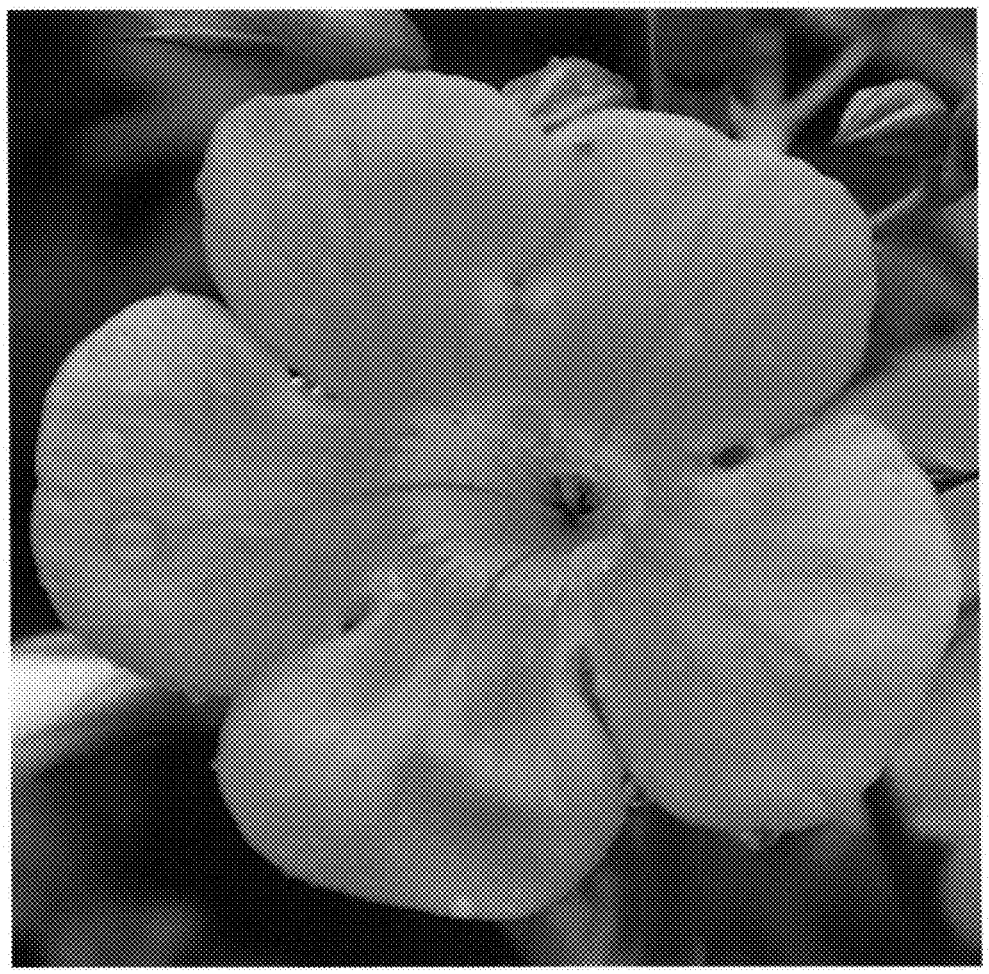

The photograph in FIG. 2 provides a close-up view of a flower of 'Takarazuka Zujin'. The colors in the photographs are as close as possible with the digital photography techniques utilized and the color values cited in the detailed botanical description accurately describe the colors of the new *Campsis*.

DETAILED BOTANICAL DESCRIPTION

The following is a detailed description of one year-old plants of the new *Campsis* as grown outdoors in one-gallon containers in Takarazuka, Japan. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

General description:

*Blooming period*.—Long bloom season, from April to August in Japan.

*Plant type*.—Perennial vine, deciduous in U.S.D.A. Zone 5.

*Plant habit*.—Very compact, upright vine.

*Height and spread*.—Reaches about 30 to 40 cm in height and 25 cm width in one year.

*Hardiness*.—At least in U.S.D.A. Zone 5.

*Diseases resistance*.—No disease resistance or susceptibility has been observed.

*Root description*.—Fibrous.

*Propagation*.—Softwood stem cuttings.

*Growth rate*.—Vigorous.

*Root description*.—Fibrous.

Stem description:

*Shape*.—Round.

*Stem color*.—Young growth; 144A, mature wood 200D.

*Stem size*.—Main stems; 30 to 40 cm in length and an average of 2.5 mm in width, lateral branches; an average of 15 cm in length and 2 mm in width.

*Stem surface*.—Glabrous.

*Internode length*.—Average of 4 cm.

*Branching*.—4 to 5 lateral branches.

Foliage description:

*Leaf division*.—Pinnately compound with 7 to 13 leaflets.

*Leaf arrangement*.—Opposite.

*Leaf attachment*.—Petiolate.

*Leaf size*.—Range from 12 to 30 cm in length and 3 to 18 cm in width.

*Leaflet size*.—Range from 2 to 10 cm in length and 1 to 4 cm in width.

*Leaflet shape*.—Elliptic to ovate-oblong.

*Leaflet base*.—Cuneate.

*Leaflet apex*.—Acuminate to long acuminate.

*Leaflet venation*.—Pinnate, not prominent, same color as leaf on mature leaves.

*Leaflet margins*.—Irregularly serrated.

*Leaflet arrangement*.—Odd pinnate.

*Leaflet attachment*.—Winged petiolules.

*Leaflet aspect*.—Slightly concave from midrib.

*Leaflet surface*.—Glabrous, smooth and moderately glossy on upper surface and glabrous, smooth and slightly glossy on lower surface.

*Leaflet color*.—New growth; 139B on upper surface and 139B lower surface, mature leaves upper surface; 139A, mature leaves lower surface; 139B.

*Petioles*.—Range from 4 to 7 cm and an average of 2.5 mm in length, 144B in color, very sparsely pubescent surface.

*Petiolules*.—An average of 7 mm in length and 1.5 mm in width, winged with base swollen, 144B in color and slightly suffused with 178B.

*Rachis*.—Average of 15 cm in length (including petiole) and an average of 2 mm in width, 144B in color and suffused with 178B, sparsely pubescent surface.

*Stipules*.—Not present.

Inflorescence description:

*Inflorescence type*.—Terminal cluster of single flowers, blooms on current year's growth.

*Inflorescence size*.—An average of 22 cm in depth and width.

*Flower buds*.—Elliptic in shape, about 2 cm in length and 1.5 cm in width, color is 20C and suffused with N30A.

*Flower fragrance*.—None noted.

*Lastingness of flowers*.—Individual flowers last about 5 to 7 days.

*Flower quantity*.—6 to 15 flowers per inflorescence are open at any one time, with up to 30 buds per inflorescence.

*Flower type*.—Tubular.

*Flower aspect*.—Upright to outward.

*Flower size*.—An average of 8 cm in length and 7 cm in diameter at apex and 5 mm in diameter at base.

*Peduncles*.—Average of 7 cm in length and 2.5 mm in diameter, 144B in color, glabrous surface, round in shape, held upright to about a 30° angle to stem (0% is vertical).

*Pedicels*.—Average of 2.5 cm in length and 2 mm in diameter, round in shape, 144B in color, glabrous surface.

*Calyx form*.—Campanulate with base fused.

*Sepals*.—5, lanceolate in shape, apiculate apex, fused base, an average of 2.5 cm in length and 5 mm in width, entire margin, color 20C and suffused with N30A, glabrous and satiny surface.

*Corolla*.—Tubular with apex flared, tube is an average of 6 cm in length and 1.4 cm in width.

*Petals*.—5, flabellate in shape with lobes rounded, upper and lower surface is smooth, margin entire to very slightly notched, fused base, round apex, about 7 cm in length with lobe portion about 3 cm in width and depth, color of upper surface when opening and mature: 30NA, color of lower surface when young and mature; a blend of 30NA and 30D, throat on inner surfaces when young and mature; a blend of 30D and 14C with veins of 30NA, color of outer surface of tubular portion a blend of 30D and 14C in color.

Reproductive organs:

*Gynoecium*.—Pistil; 1, about 5 mm in length, 26D in color.

*Androcoecium*.—Stamens; 4, anthers; narrowly elliptic in shape, an average of 3 cm in length, 18c in color, pollen; moderate in quantity and 11D in color.

*Seed*.—Not observed.

It is claimed:

1. A new and distinct cultivar of *Campsis* plant named 'Takarazuka Zujin' as herein illustrated and described.

* * * * *